United States Patent
Lu et al.

(10) Patent No.: US 12,378,192 B2
(45) Date of Patent: Aug. 5, 2025

(54) CRYSTALLINE FORM OF CAPSID PROTEIN ASSEMBLY INHIBITOR CONTAINING N HETERO FIVE-MEMBERED RING, AND APPLICATION THEREOF

(71) Applicant: CHIA TAI TIANQING PHARMACEUTICAL GROUP CO., LTD., Lianyungang (CN)

(72) Inventors: Yin Lu, Lianyungang (CN); Meng Guo, Lianyungang (CN); Mingtong Hu, Lianyungang (CN); Yuan Li, Lianyungang (CN); Wangwei Ao, Lianyungang (CN); Yinsheng Zhang, Lianyungang (CN)

(73) Assignee: CHIA TAI TIANQING PHARMACEUTICAL GROUP CO., LTD., Lianyungang (CN)

( * ) Notice: Subject to any disclaimer, the term of this patent is extended or adjusted under 35 U.S.C. 154(b) by 800 days.

(21) Appl. No.: 17/764,519

(22) PCT Filed: Sep. 28, 2020

(86) PCT No.: PCT/CN2020/118427
§ 371 (c)(1),
(2) Date: Mar. 28, 2022

(87) PCT Pub. No.: WO2021/058002
PCT Pub. Date: Apr. 1, 2021

(65) Prior Publication Data
US 2022/0363634 A1 Nov. 17, 2022
US 2023/0212117 A2 Jul. 6, 2023

(30) Foreign Application Priority Data

Sep. 29, 2019 (CN) .......................... 201910934549.0

(51) Int. Cl.
C07D 207/34 (2006.01)

(52) U.S. Cl.
CPC ........ *C07D 207/34* (2013.01); *C07B 2200/13* (2013.01)

(58) Field of Classification Search
CPC .......................... C07D 207/34; C07B 2200/13
See application file for complete search history.

(56) References Cited

U.S. PATENT DOCUMENTS

| | | | |
|---|---|---|---|
| 2021/0017154 A1 | 1/2021 | Zhang et al. | |
| 2021/0017184 A1* | 1/2021 | Zheng | A61K 9/0053 |
| 2022/0185774 A1 | 6/2022 | Zhang et al. | |

FOREIGN PATENT DOCUMENTS

| | | |
|---|---|---|
| CN | 105658624 A | 6/2016 |
| CN | 107721895 A | 2/2018 |
| CN | 109790168 A | 5/2019 |
| EP | 3915972 A1 | 12/2021 |
| RU | 2007107388 A | 9/2008 |
| WO | 2006012642 A2 | 2/2006 |
| WO | 2014/184350 A1 | 11/2014 |
| WO | 2015/011281 A1 | 1/2015 |
| WO | 2015/059212 A1 | 4/2015 |
| WO | 2015/118057 A1 | 8/2015 |
| WO | 2017/156255 A1 | 9/2017 |
| WO | 2018/039531 A1 | 3/2018 |
| WO | 2018/050110 A1 | 3/2018 |
| WO | 2019/165374 A1 | 8/2019 |
| WO | 2020/151252 A1 | 9/2019 |
| WO | 2019/185016 A1 | 10/2019 |
| WO | 2019/241292 A1 | 12/2019 |
| WO | 2021/058001 A1 | 4/2021 |

OTHER PUBLICATIONS

Testa, Bernard; "Prodrug research: futile or fertile?," Biochemical Pharmacology 68; 2097-2106, 2004.
Non-Final Office Action for U.S. Appl. No. 17/425,701, dated Jun. 3, 2024, 37 pages.
Brahmania, et al; New therapeutic agents for chronic hepatitis B; Review—Lancet Infect. Dis.; Jan. 2016; pp. 1-12.
He, et al; Hepatitis B virus replication mechanisms and drug targets of chronic hepatitis B; Chinese Pharmacological Bulletin; Feb. 2015; 31(2):152-6 (Abstract on p. 156).
Wuts, et al; Protection for the Hydroxyl Group, Including 1,2-and 1,3-Diols; Greene's Protective Groups in Organic Synthesis; 4th Ed.; 2007; pp. 16-366.
Alekseyev, Optical Isomerism and Drugs Pharmacological Activity, Soros Educational Journal, 1998, pp. 49-55.

(Continued)

*Primary Examiner* — Timothy R Rozof
(74) *Attorney, Agent, or Firm* — Kilpatrick Townsend & Stockton LLP

(57) ABSTRACT

Disclosed by the present application is a crystalline form of a capsid protein assembly inhibitor containing an N hetero five-membered ring; specifically disclosed is the crystalline form of the compound of formula I; also comprised is an the application of said crystalline form in the preparation of a drug for preventing or treating diseases benefiting from the inhibition of capsid protein assembly.

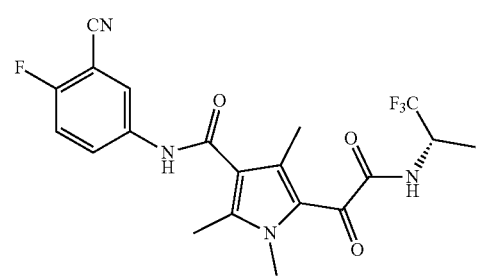

18 Claims, 2 Drawing Sheets

(56) References Cited

OTHER PUBLICATIONS

Knunyants, Chemical Encyclopedic Dictionary, Moscow, Soviet Encyclopedia, 1983, pp. 130-131.
Kummerer, Pharmaceuticals in the environment; Annual Review of Environment and Resources; 2010, v.35, pp. 57-75, doi: 10.1146/annurev-environ-052809-161223.
Patent Office of the Russian Federation, Office Action of Application No. 2021123614/04(049497), dated Feb. 28, 2023, 27 pages with translation.
Nozaki, et al; Medicinal Drug Chemistry (Soyaku Kagaku); Jul. 1, 1995; 8 pgs.
China National Intellectual Property Administration (ISA/CN); International Search Report of PCT/CN2020/118427; mailed Dec. 31, 2020; 8 pgs.

* cited by examiner

CRYSTALLINE FORM OF CAPSID PROTEIN ASSEMBLY INHIBITOR CONTAINING N HETERO FIVE-MEMBERED RING, AND APPLICATION THEREOF

CROSS-REFERENCE TO RELATED APPLICATIONS

The present application is a § 371 National Phase Application of PCT/CN2020/118427, filed Sep. 28, 2020, which application claims priority and benefit to the Chinese Patent Application No. 201910934549.0 filed with National Intellectual Property Administration, PRC on Sep. 29, 2019, the disclosures of which are incorporated herein by reference in their entireties for all purposes herein.

TECHNICAL FIELD

The present application relates to a crystalline form of a capsid protein assembly inhibitor containing a five-membered N heterocycle, and in particular, to a crystalline form of a compound of formula I. The present application also relates to use of the crystalline form in preparing a medicament for preventing or treating a disease benefiting from capsid protein assembly inhibition.

BACKGROUND

Currently, since there is only control for chronic viral hepatitis B rather than curative measures, treatments are restricted to two groups of agents (interferon and nucleoside analogues/inhibitors of viral polymerase). The low cure rate of HBV is partly due to the presence and persistence of covalently closed circular DNA (cccDNA) in the nuclei of infected hepatocytes. Current treatments cannot eliminate the cccDNA in the reservoir, while some new targets of HBV, such as core inhibitors (e.g., inhibitors of viral capsid protein formation or assembly, cccDNA inhibitors and activators of interferon-stimulated genes, etc.), are promising for curing hepatitis B (Mayur Brahmania, et al., New therapeutic agents for chronic hepatitis B). The HBV capsid is assembled from the core protein, and before reverse transcription, HBV reverse transcriptase and pgRNA should be correctly encapsulated by the capsid protein. Thus, blocking capsid protein assembly or accelerating capsid protein degradation can block the process of capsid protein assembly, thereby affecting virus replication.

BRIEF SUMMARY

In one aspect, the present application provides a crystalline form of a compound of formula I,

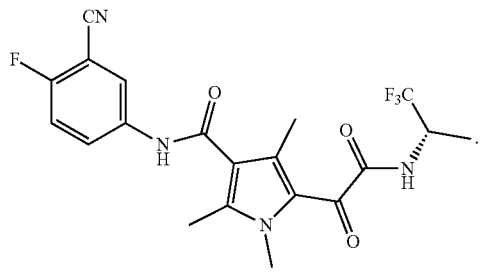

I

In another aspect, the present application provides a crystalline form composition, wherein the crystalline form of the compound of formula I disclosed herein accounts for 50% or more, preferably 80% or more, more preferably 90% or more and most preferably 95% or more of the weight of the crystalline form composition.

In another aspect, the present application provides a pharmaceutical composition comprising a therapeutically effective amount of the crystalline form of the compound of formula I or the crystalline form composition thereof disclosed herein.

In still another aspect, the present application also provides use of the crystalline form of the compound of formula I, the crystalline form composition thereof or the pharmaceutical composition thereof disclosed herein in preparing a medicament for preventing or treating a disease benefiting from capsid protein assembly inhibition.

In still another aspect, the present application also provides use of the crystalline form of the compound of formula I, the crystalline form composition thereof or the pharmaceutical composition thereof disclosed herein in preparing a medicament for preventing or treating hepatitis B virus infection.

In still another aspect, the present application also provides use of the crystalline form of the compound of formula I, the crystalline form composition thereof or the pharmaceutical composition thereof disclosed herein in preventing or treating a disease benefiting from capsid protein assembly inhibition.

In still another aspect, the present application also provides a method for preventing or treating a disease benefiting from capsid protein assembly inhibition, comprising administering to a mammal in need of such prevention or treatment a therapeutically effective amount of the crystalline form of the compound of formula I, the crystalline form composition thereof or the pharmaceutical composition thereof disclosed herein.

In still another aspect, the present application also provides the crystalline form of the compound of formula I, the crystalline form composition thereof or the pharmaceutical composition thereof disclosed herein for use in preventing or treating a disease benefiting from capsid protein assembly inhibition.

SUMMARY

Figure 1:
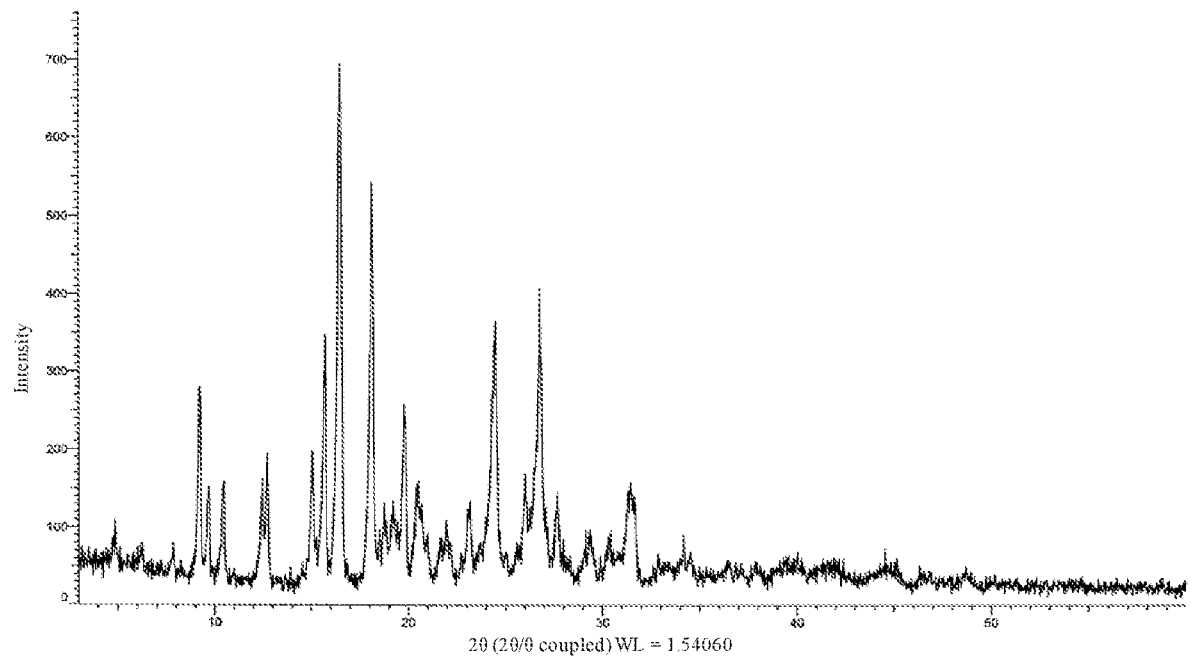
FIG. 1 is an XRPD pattern of a crystalline form I of the compound of formula I.

In one aspect, the present application provides a crystalline form of a compound of formula I,

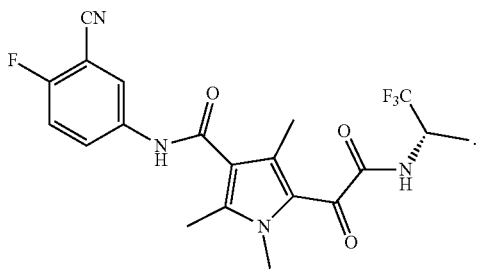

In another aspect, the present application provides a crystalline form I of the compound of formula I described above having characteristic diffraction peaks in an X-ray powder diffraction pattern at the following 2θ: 9.21±0.20°, 16.47±0.20°, 18.11±0.20°, 24.48±0.20° and 26.79±0.20°; in some embodiments of the present application, the crystalline form I described above has characteristic diffraction peaks in an X-ray powder diffraction pattern at the following 2θ: 9.21±0.20°, 12.72±0.20°, 15.71±0.20°, 16.47±0.20°, 18.11±0.20°, 19.79±0.20°, 24.48±0.20° and 26.79±0.20°; in some embodiments of the present application, the crystalline form I described above has characteristic diffraction peaks in an X-ray powder diffraction pattern at the following 2θ: 9.21±0.20°, 10.44±0.20°, 12.72±0.20°, 15.06±0.20°, 15.71±0.20°, 16.47±0.20°, 18.11±0.20°, 19.79±0.20°, 20.46±0.20°, 24.48±0.20°, 26.79±0.20° and 31.46±0.20°; in some embodiments of the present application, the crystalline form I described above has characteristic diffraction peaks in an X-ray powder diffraction pattern at the following 2θ: 9.21±0.20°, 9.68±0.20°, 10.44±0.20°, 12.72±0.20°, 15.06±0.20°, 15.71±0.20°, 16.47±0.20°, 18.11±0.20°, 19.79±0.20°, 20.46±0.20°, 24.48±0.20°, 26.02±0.20°, 26.79±0.20°, 27.67±0.20° and 31.46±0.20°; in some embodiments of the present application, the crystalline form I described above has characteristic diffraction peaks in an X-ray powder diffraction pattern at the following 2θ: 4.86±0.20°, 9.21±0.20°, 9.68±0.20°, 10.44±0.20°, 12.47±0.20°, 12.72±0.20°, 15.06±0.20°, 15.71±0.20°, 16.47±0.20°, 18.11±0.20°, 18.74±0.20°, 19.19±0.20°, 19.79±0.20°, 20.46±0.20°, 20.94±0.20°, 21.65±0.20°, 21.96±0.20°, 23.12±0.20°, 24.48±0.20°, 26.02±0.20°, 26.79±0.20°, 27.67±0.20°, 29.36±0.20°, 31.46±0.20° and 34.17±0.20°.

In some embodiments of the present application, the positions and relative intensities of diffraction peaks in the XRPD pattern of the crystalline form I described above are shown in Table 1 below:

TABLE 1

XRPD data for crystalline form I

| No. | 2θ (±0.20°) | Relative intensity (%) |
|---|---|---|
| 1 | 4.86 | 6.3 |
| 2 | 6.19 | 2.9 |
| 3 | 7.84 | 4.1 |
| 4 | 9.21 | 37.1 |
| 5 | 9.68 | 17.0 |
| 6 | 10.44 | 18.5 |
| 7 | 12.47 | 18.4 |
| 8 | 12.72 | 23.9 |
| 9 | 15.06 | 22.9 |
| 10 | 15.71 | 45.2 |
| 11 | 16.47 | 100 |
| 12 | 18.11 | 73.8 |
| 13 | 18.74 | 11.5 |
| 14 | 19.19 | 11.8 |
| 15 | 19.79 | 30.6 |
| 16 | 20.46 | 16.4 |
| 17 | 20.94 | 6.7 |
| 18 | 21.65 | 6.2 |
| 19 | 21.96 | 9.1 |
| 20 | 23.12 | 11.0 |
| 21 | 24.48 | 47.5 |
| 22 | 26.02 | 15.6 |
| 23 | 26.79 | 48.1 |
| 24 | 27.67 | 12.7 |
| 25 | 29.36 | 7.4 |
| 26 | 30.38 | 5.7 |
| 27 | 31.46 | 17.5 |
| 28 | 34.17 | 6.8 |
| 29 | 34.53 | 5.0 |

In some embodiments of the present application, the X-ray powder diffraction pattern (XRPD) of the crystalline form I described above is shown in FIG. 1.

In some embodiments of the present application, the crystalline form I described above has an endothermic peak in a differential scanning calorimetry (DSC) curve at 231.26±5° C.

In some embodiments of the present application, the DSC pattern of the crystalline form I described above is shown in FIG. 2.

In still another aspect, the present application provides a method for preparing the crystalline form I, the method comprising:

adding the compound of formula I described above to a solvent, and separating a solid.

In some embodiments of the present application, the method for preparing crystalline form I described above comprises: adding the compound of formula I described above to a solvent, crystallizing and separating a solid.

In some embodiments of the present application, in the method for preparing the crystalline form I described above, the solvent is selected from the group consisting of mixtures of one or more of methanol, acetonitrile or water. In some embodiments of the present application, in the method for preparing the crystalline form I described above, the solvent is selected from the group consisting of methanol or a mixture of acetonitrile and water.

In some embodiments of the present application, in the method for preparing the crystalline form I described above, the volume-to-mass ratio of the solvent to the compound of formula I is 1-100 mL/g; in some embodiments of the present application, the volume-to-mass ratio of the solvent to the compound of formula I is 1 mL/g, 5 mL/g, 10 mL/g, 15 mL/g, 20 mL/g, 25 mL/g, 30 mL/g, 35 mL/g, 40 mL/g, 45 mL/g, 50 mL/g, 55 mL/g, 60 mL/g, 65 mL/g, 70 mL/g, 75 mL/g, 80 mL/g, 85 mL/g, 90 mL/g, 100 mL/g or within a range formed by any of the ratios.

In some embodiments of the present application, in the method for preparing the crystalline form I described above, the volume-to-mass ratio of methanol to the compound of formula I is 1-20 mL/g; in some embodiments of the present application, the volume-to-mass ratio of methanol to the compound of formula I is 1 mL/g, 2 mL/g, 3 mL/g, 4 mL/g, 5 mL/g, 6 mL/g, 7 mL/g, 8 mL/g, 9 mL/g, 10 mL/g, 11 mL/g, 12 mL/g, 13 mL/g, 14 mL/g, 15 mL/g, 16 mL/g, 17 mL/g, 18 mL/g, 19 mL/g, 20 mL/g or within a range formed by any of the ratios; in some embodiments of the present application, the volume-to-mass ratio of methanol to the compound of formula I is 1-10 mL/g or 2-8 mL/g; in some embodiments of the present application, the volume-to-mass ratio of methanol to the compound of formula I is 5 mL/g.

In some embodiments of the present application, in the method for preparing the crystalline form I described above, the volume-to-mass ratio of acetonitrile to the compound of formula I is 1-20 mL/g; in some embodiments of the present application, the volume-to-mass ratio of acetonitrile to the compound of formula I is 1 mL/g, 2 mL/g, 3 mL/g, 4 mL/g, 5 mL/g, 6 mL/g, 7 mL/g, 8 mL/g, 9 mL/g, 10 mL/g, 11 mL/g, 12 mL/g, 13 mL/g, 14 mL/g, 15 mL/g, 16 mL/g, 17 mL/g, 18 mL/g, 19 mL/g, 20 mL/g or within a range formed by any of the ratios; in some embodiments of the present application, the volume-to-mass ratio of acetonitrile to the compound of formula I is 5-18 mL/g or 8-16 mL/g; in some embodiments of the present application, the volume-to-mass ratio of acetonitrile to the compound of formula I is 12.5 mL/g.

In some embodiments of the present application, in the method for preparing the crystalline form I described above, the volume ratio of acetonitrile to water is 1:1-1:10; in some embodiments of the present application, the volume ratio of acetonitrile to water is 1:1, 1:2, 1:3, 1:4, 1:5, 1:6, 1:7, 1:8, 1:9, 1:10, or within a range formed by any of the ratios; in some embodiments of the present application, the volume ratio of acetonitrile to water is 1:1-1:5; in some embodiments of the present application, the volume ratio of acetonitrile to water is 1:5.

In some embodiments of the present application, in the method for preparing the crystalline form I described above, the means for separating the solid is selected from filtration.

In some embodiments of the present application, the method for preparing the crystalline form I described above comprises: adding the compound of formula I described above to a solvent, and stirring to give a clarified solution or optionally, heating to give a clarified solution.

In some embodiments of the present application, the method for preparing the crystalline form I described above optionally comprises cooling to room temperature and/or cooling in an ice-water bath for crystallization, and/or optionally adding water for crystallization.

In another aspect, the present application further provides a crystalline form II of the compound of formula I described above having characteristic diffraction peaks in an X-ray powder diffraction pattern at the following 2θ: 14.09±0.20°, 15.81±0.20°, 17.40±0.20°, 18.81±0.20° and 22.91±0.20°; in some embodiments of the present application, the crystalline form II described above has characteristic diffraction peaks in an X-ray powder diffraction pattern at the following 2θ: 8.45±0.20°, 13.35±0.20°, 14.09±0.20°, 14.90±0.20°, 15.81±0.20°, 17.40±0.20°, 18.81±0.20°, 19.64±0.20° and 22.91±0.20°; in some embodiments of the present application, the crystalline form II described above has characteristic diffraction peaks in an X-ray powder diffraction pattern at the following 2θ: 8.45±0.20°, 11.15±0.20°, 13.35±0.20°, 14.09±0.20°, 14.90±0.20°, 15.81±0.20°, 17.40±0.20°, 18.81±0.20°, 19.64±0.20°, 20.97±0.20°, 22.91±0.20°, 23.68±0.20° and 25.24±0.20°; in some embodiments of the present application, the crystalline form II described above has characteristic diffraction peaks in an X-ray powder diffraction pattern at the following 2θ: 8.45±0.20°, 11.15±0.20°, 13.35±0.20°, 14.09±0.20°, 14.90±0.20°, 15.81±0.20°, 17.40±0.20°, 18.81±0.20°, 19.64±0.20°, 20.25±0.20°, 20.97±0.20°, 21.42±0.20°, 22.91±0.20°, 23.68±0.20°, 25.24±0.20°, 27.72±0.20° and 30.00±0.20°; in some embodiments of the present application, the crystalline form II described above has characteristic diffraction peaks in an X-ray powder diffraction pattern at the following 2θ: 4.74±0.20°, 7.94±0.20°, 8.45±0.20°, 9.40±0.20°, 9.91±0.20°, 11.15±0.20°, 13.35±0.20°, 14.09±0.20°, 14.90±0.20°, 15.81±0.20°, 17.40±0.20°, 18.81±0.20°, 19.64±0.20°, 20.25±0.20°, 20.97±0.20°, 21.42±0.20°, 22.91±0.20°, 23.68±0.20°, 25.24±0.20°, 27.72±0.20° and 30.00±0.20°.

In some embodiments of the present application, the positions and relative intensities of diffraction peaks in the XRPD pattern of the crystalline form II described above are shown in Table 2 below:

TABLE 2

XRPD data for crystalline form II

| No. | 2θ (±0.20°) | Relative intensity (%) |
|---|---|---|
| 1 | 4.74 | 8.3 |
| 2 | 7.94 | 9.9 |
| 3 | 8.45 | 11.9 |
| 4 | 9.40 | 6.2 |
| 5 | 9.91 | 9.2 |
| 6 | 11.15 | 13.6 |
| 7 | 13.35 | 29.6 |
| 8 | 14.09 | 100.0 |
| 9 | 14.90 | 33.0 |
| 10 | 15.81 | 70.9 |
| 11 | 17.40 | 86.5 |
| 12 | 18.81 | 59.6 |
| 13 | 19.64 | 23.7 |
| 14 | 20.25 | 17.4 |
| 15 | 20.97 | 19.2 |
| 16 | 21.42 | 12.3 |
| 17 | 22.91 | 50.0 |
| 18 | 23.26 | 31.8 |
| 19 | 23.68 | 21.1 |
| 20 | 25.13 | 15.0 |
| 21 | 25.24 | 20.9 |
| 22 | 27.72 | 18.4 |
| 23 | 30.00 | 11.9 |
| 24 | 30.90 | 8.1 |
| 25 | 32.71 | 7.0 |
| 26 | 34.12 | 7.6 |

In some embodiments of the present application, the X-ray powder diffraction pattern (XRPD) of the crystalline form II described above is shown in FIG. 3.

In some embodiments of the present application, the crystalline form II described above has an endothermic peak in a differential scanning calorimetry (DSC) curve at 225.05±5° C.

In some embodiments of the present application, the DSC pattern of the crystalline form II described above is shown in FIG. 4.

In still another aspect, the present application provides a method for preparing the crystalline form II, the method comprising: adding the compound of formula I to a solvent, and precipitating a solid.

In some embodiments, in the method for preparing the crystalline form II described above, the solvent is selected from the group consisting of mixtures of one or more of acetone, tetrahydrofuran or water. In some embodiments, in the method for preparing the crystalline form II described above, the solvent is selected from the group consisting of a mixture of acetone and water or a mixture of tetrahydrofuran and water.

In some embodiments of the present application, in the method for preparing the crystalline form II described above, the volume-to-mass ratio of the solvent to the compound of formula I is 1-100 mL/g; in some embodiments of the present application, the volume-to-mass ratio of the solvent to the compound of formula I is 1 mL/g, 5 mL/g, 10 mL/g, 15 mL/g, 20 mL/g, 25 mL/g, 30 mL/g, 35 mL/g, 40 mL/g, 45 mL/g, 50 mL/g, 55 mL/g, 60 mL/g, 65 mL/g, 70 mL/g, 75 mL/g, 80 mL/g, 85 mL/g, 90 mL/g, 100 mL/g or within a range formed by any of the ratios.

In some embodiments of the present application, in the method for preparing the crystalline form II described above, the volume-to-mass ratio of acetone to the compound of formula I is 1-50 mL/g; in some embodiments of the present application, the volume-to-mass ratio of acetone to the compound of formula I is 1 mL/g, 5 mL/g, 10 mL/g, 15 mL/g, 20 mL/g, 25 mL/g, 30 mL/g, 35 mL/g, 40 mL/g, 45 mL/g, 50 mL/g or within a range formed by any of the ratios; in some embodiments of the present application, the volume-to-mass ratio of acetone to the compound of formula I is 5-40 mL/g or 10-30 mL/g; in some embodiments of the present application, the volume-to-mass ratio of acetone to the compound of formula I is 20 mL/g.

In some embodiments of the present application, in the method for preparing the crystalline form II described above, the volume ratio of acetone to water is 1:0.5-1:5; in some embodiments of the present application, the volume ratio of acetone to water is 1:0.5, 1:1, 1:1.5, 1:2, 1:2.5, 1:3, 1:3.5, 1:4, 1:4.5, 1:5, or within a range formed by any of the ratios; in some embodiments of the present application, the volume ratio of acetone to water is 1:0.5-1:2; in some embodiments of the present application, the volume ratio of acetone to water is 1:1.25.

In some embodiments, in the method for preparing the crystalline form II described above, after precipitating the solid, filtration may be selected to separate the solid.

In some embodiments of the present application, the method for preparing the crystalline form II described above comprises: adding the compound of formula I described above to a solvent, and stirring to give a clarified solution or optionally, heating to give a clarified solution.

In some embodiments of the present application, the method for preparing the crystalline form II described above optionally comprises cooling to room temperature and/or cooling in an ice-water bath for crystallization, and/or optionally adding water for crystallization.

In some specific embodiments, the method for preparing the crystalline form I or the crystalline form II described above further comprises drying the separated solid, for example, drying at 30-90° C., or drying at 50-60° C.

In the present application, XRPD is performed by a Bruker D8 ADVANCE X-ray powder diffractometer, light tube: Cu, k α (λ=1.54056 Å), light tube voltage: 40 kV, light tube current: 40 mA; scattering slit: 0.618 mm; scanning range: 3-60 deg; step size: 0.02 deg; step time: 0.1 s.

In the present application, DSC is performed by a Mettler DSC 1 differential scanning calorimeter, 50-300° C., heating rate: 10.00 K/min.

In another aspect, the present application provides a crystalline form composition, wherein the crystalline form of the compound of formula I disclosed herein accounts for 50% or more, preferably 80% or more, more preferably 90% or more and most preferably 95% or more of the weight of the crystalline form composition.

In another aspect, the present application provides a crystalline form composition comprising the crystalline form I and/or the crystalline form II described above, wherein the crystalline form I and/or the crystalline form II account for 50% or more, preferably 80% or more, more preferably 90% or more and most preferably 95% or more of the weight of the crystalline form composition.

In another aspect, the present application provides a pharmaceutical composition comprising a therapeutically effective amount of the crystalline form of the compound of formula I or the crystalline form composition thereof disclosed herein. The pharmaceutical composition disclosed herein may or may not contain a pharmaceutically acceptable excipient. In addition, the pharmaceutical composition disclosed herein may further comprise one or more additional therapeutic agents.

In still another aspect, the present application also provides use of the crystalline form of the compound of formula I, the crystalline form composition thereof or the pharmaceutical composition thereof disclosed herein in preparing a medicament for preventing or treating a disease benefiting from capsid protein assembly inhibition.

In still another aspect, the present application also provides use of the crystalline form of the compound of formula I, the crystalline form composition thereof or the pharmaceutical composition thereof disclosed herein in preparing a medicament for preventing or treating hepatitis B virus infection.

In still another aspect, the present application also provides use of the crystalline form of the compound of formula I, the crystalline form composition thereof or the pharmaceutical composition thereof disclosed herein in preventing or treating a disease benefiting from capsid protein assembly inhibition.

In still another aspect, the present application also provides a method for preventing or treating a disease benefiting from capsid protein assembly inhibition, comprising administering to a mammal, preferably a human, in need of such treatment or prevention a therapeutically effective amount of the crystalline form of the compound of formula I, the crystalline form composition thereof or the pharmaceutical composition thereof disclosed herein.

In still another aspect, the present application also provides the crystalline form of the compound of formula I, the crystalline form composition thereof or the pharmaceutical composition thereof disclosed herein for use in preventing or treating a disease benefiting from capsid protein assembly inhibition.

As used herein, the crystalline form of the compound of formula I disclosed herein is selected from the group consisting of the crystalline form of the compound of formula I, the crystalline form I of the compound of formula I, the crystalline form II of the compound of formula I, and a mixture of the crystalline form I and the crystalline form II of the compound of formula I.

In some embodiments of the present application, the disease benefiting from capsid protein assembly inhibition is a disease caused by hepatitis B virus (HBV) infection.

In some embodiments of the present application, the disease benefiting from capsid protein assembly inhibition is a liver disease caused by hepatitis B virus (HBV) infection.

In some embodiments of the present application, the prevention or treatment of the disease benefiting from capsid protein assembly inhibition refers to control, reduction or elimination of HBV to prevent, alleviate or cure a liver disease in an infected patient.

Definitions and Description

Unless otherwise stated, the following terms and phrases used herein are intended to have the following meanings.

A particular phrase or term, unless otherwise specifically defined, should not be considered as uncertain or unclear, but construed according to its common meaning. When referring to a trade name, it is intended to refer to its corresponding commercial product or its active ingredient.

It should be noted that in the X-ray powder diffraction pattern, the position and relative intensity of a peak may vary due to measuring instruments, measuring methods/conditions, and other factors. For any specific crystalline form, the position of a peak may have an error, and the measurement of 2θ may have an error of ±0.20°.

Therefore, this error should be considered when determining each crystalline form, and crystalline forms within this margin of error are within the scope of the present application.

It should be noted that, for the same crystalline form, the position of an endothermic peak in the DSC pattern may vary due to measuring instruments, measuring methods/conditions, and other factors. For any specific crystalline form, the position of an endothermic peak may have an error of ±5° C. or ±3° C. Therefore, this error should be considered when determining each crystalline form, and crystalline forms within this margin of error are within the scope of the present application.

The word "comprise" and variations thereof such as "comprises" or "comprising" will be understood in an open, non-exclusive sense, i.e., "including but not limited to".

The term "pharmaceutically acceptable excipient" refers to an inert substance administered with active ingredient to facilitate administration of the active ingredient, including, but not limited to, any glidant, sweetener, diluent, preservative, dye/coloring agent, flavor enhancer, surfactant, wetting agent, dispersant, disintegrant, suspending agent, stabilizer, isotonizing agent, solvent or emulsifier acceptable for use in humans or animals (e.g., domesticated animals) as permitted by the National Medical Products Administration, PRC. Non-limiting examples of the excipients include calcium carbonate, calcium phosphate, various sugars and types of starch, cellulose derivatives, gelatin, vegetable oils, and polyethylene glycols.

The term "pharmaceutical composition" refers to a mixture consisting of one or more of the compounds or pharmaceutically acceptable salts thereof disclosed herein and a pharmaceutically acceptable excipient. The pharmaceutical composition is intended to facilitate the administration of the compound to an organic entity.

The pharmaceutical composition disclosed herein can be prepared by combining the compound disclosed herein with a suitable pharmaceutically acceptable excipient, and can be formulated, for example, into a solid, semisolid, liquid, or gaseous formulation such as tablet, pill, capsule, powder, granule, ointment, emulsion, suspension, suppository, injection, inhalant, gel, microsphere, and aerosol.

Typical routes of administration of the crystalline form or the pharmaceutical composition thereof disclosed herein include, but are not limited to, oral, rectal, topical, inhalation, parenteral, sublingual, intravaginal, intranasal, intraocular, intraperitoneal, intramuscular, subcutaneous and intravenous administrations.

The pharmaceutical composition disclosed herein can be manufactured by methods well known in the art, such as conventional mixing, dissolving, granulating, dragee-making, levigating, emulsifying, and lyophilizing.

In some embodiments, the pharmaceutical composition is in an oral form. For oral administration, the pharmaceutical composition can be formulated by mixing the active compounds with pharmaceutically acceptable excipients well known in the art. These excipients enable the compounds disclosed herein to be formulated into tablets, pills, pastilles, dragees, capsules, liquids, gels, slurries, suspensions and the like for oral administration to a patient.

Therapeutic dosages of the compounds disclosed herein may be determined by, for example, the specific use of a treatment, the route of administration of the compound, the health and condition of a patient, and the judgment of a prescribing physician. The proportion or concentration of the compound disclosed herein in a pharmaceutical composition may not be constant and depends on a variety of factors including dosages, chemical properties (e.g., hydrophobicity), and routes of administration. The term "treat" or "treatment" means administering the compound or formulation described herein to ameliorate or eliminate a disease or one or more symptoms associated with the disease, and includes:

(i) inhibiting a disease or disease state, i.e., arresting its development; and (ii) alleviating a disease or disease state, i.e., causing its regression.

The term "prevent" or "prevention" means administering the compound or formulation described herein to prevent a disease or one or more symptoms associated with the disease, and includes: preventing the occurrence of the disease or disease state in a mammal, particularly when such a mammal is predisposed to the disease state but has not yet been diagnosed with it.

For drugs and pharmacological active agents, the term "therapeutically effective amount" refers to an amount of a drug or a medicament that is sufficient to provide the desired effect but is non-toxic. The determination of the effective amount varies from person to person. It depends on the age and general condition of a subject, as well as the particular active substance used. The appropriate effective amount in a case may be determined by those skilled in the art in the light of routine tests.

The therapeutically effective amount of the crystalline form disclosed herein is from about 0.0001 to 20 mg/kg body weight (bw)/day, for example from 0.001 to 10 mg/kg bw/day.

The dosage frequency of the crystalline form disclosed herein depends on needs of an individual patient, e.g., once or twice daily or more times daily. Administration may be intermittent, for example, in a period of several days, the patient receives a daily dose of the crystalline form, and in a following period of several days or more days, the patient does not receive the daily dose of the crystalline form.

All solvents used in the present application are commercially available and can be used without further purification.

The following abbreviations are used herein: DMF for N,N-dimethylformamide; PE for petroleum ether; EA for ethyl acetate; DMSO for dimethyl sulfoxide; THF for tetrahydrofuran; DCM for dichloromethane; HATU for 2-(7-benzotriazole oxide)-N,N,N',N'-tetramethyluronium hexafluorophosphate; DIPEA for N,N-diisopropylethylamine.

Technical Effects

The crystalline form of the present application has good pharmacological activity and good stability under conditions of high humidity, high temperature or illumination, demonstrating good pharmaceutical properties and high druggability prospect.

DETAILED DESCRIPTION

The present application is described in detail below by way of examples. However, this is by no means disadvantageously limiting the scope of the present application. Although the present application has been described in detail herein and specific embodiments have also been disclosed, it will be apparent to those skilled in the art that various changes and modifications can be made to the specific embodiments without departing from the spirit and scope of the present application.

Example 1. Preparation of Compound of Formula I

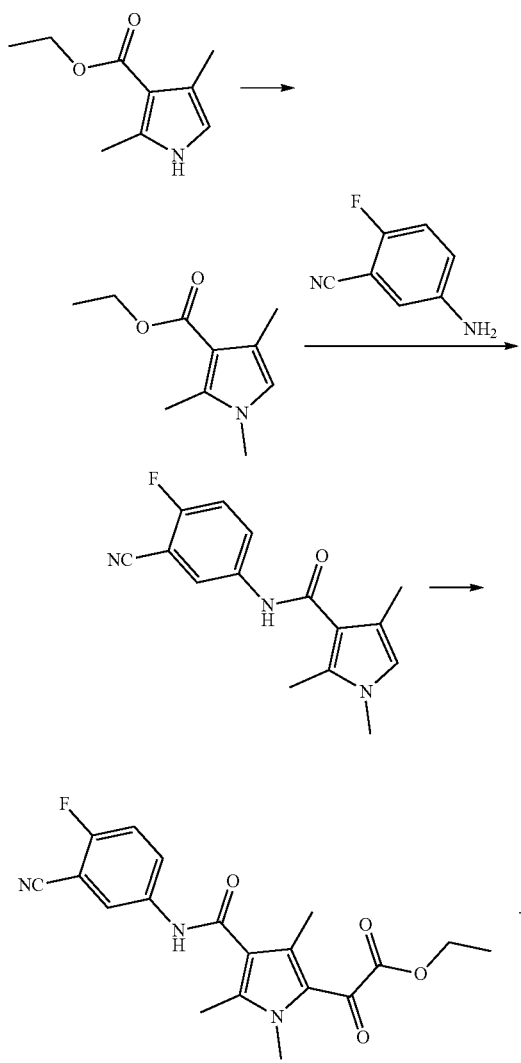

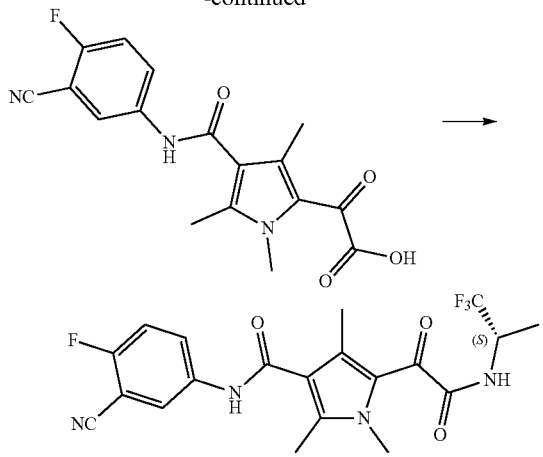

-continued

Step A: DMF (100 mL), ethyl 2,4-dimethyl-1H-pyrrol-3-carboxylate (8.0 g) and iodomethane (8.15 g) were added to a 500 mL single-neck flask under nitrogen atmosphere. Sodium hydride (2.87 g) was added in portions in an ice bath. After the addition, the reaction system was warmed to room temperature and reacted for 2.5 h. After the reaction was completed, the mixture was slowly poured into 400 mL of ice water to quench the reaction and extracted with ethyl acetate (2×300 mL). The organic phases were combined, washed with saturated aqueous sodium chloride solution, and dried over anhydrous sodium sulfate. The solvent was removed by evaporation at reduced pressure. The resulting crude product was separated by silica gel column chromatography (PE:EA=20:1) to obtain ethyl 1,2,4-trimethyl-1H-pyrrol-3-carboxylate (4.87 g). $^1$H-NMR (500 MHz, DMSO-$d_6$): δ 6.44 (s, 1H), 4.15 (q, J=7.5 Hz, 2H), 3.44 (s, 3H), 2.39 (s, 3H), 2.09 (s, 3H), 1.25 (t, J=7.0 Hz, 3H). $^{13}$C-NMR (125 MHz, DMSO-$d_6$): δ 165.63, 136.13, 120.78, 118.91, 110.56, 58.76, 33.58, 14.85, 12.93, 11.60. MS (ESI+, [M+H]$^+$) m/z: 182.3.

Step B: THF (150 mL), ethyl 1,2,4-trimethyl-1H-pyrrol-3-carboxylate (15.0 g) and 5-amino-2-fluorobenzonitrile (14.08 g) were added to a 500 mL three-necked flask under nitrogen atmosphere. Lithium bis(trimethylsilyl)amide (27.7 g, in 166 mL of THF) was slowly and dropwise added in an ice bath. After the addition, the reaction system was warmed to room temperature and reacted for 16.0 h. After the reaction was completed, the mixture was slowly poured into 500 mL of ice water to quench the reaction and extracted with ethyl acetate (2×400 mL). The organic phases were combined, washed with saturated aqueous sodium chloride solution and dried over anhydrous sodium sulfate. The solvent was removed by evaporation at reduced pressure. The resulting crude product was separated by silica gel column chromatography (PE:EA=1:1) to obtain N-(3-cyano-4-fluorophenyl)-1,2,4-trimethyl-1H-pyrrol-3-carboxamide (6.73 g). $^1$H-NMR (500 MHz, DMSO-$d_6$): δ 9.64 (s, 1H), 8.18 (t, J=3.5 Hz, 1H), 7.93-7.96 (m, 1H), 7.48 (t, J=9.0 Hz, 1H), 6.49 (s, 1H), 3.47 (s, 3H), 2.30 (s, 3H), 2.10 (s, 3H). $^{13}$C-NMR (125 MHz, DMSO-$d_6$): δ 165.51, 159.30, 157.15, 137.56, 131.76, 126.97, 123.33, 120.33, 117.39, 116.77, 114.59, 10±0.19, 33.53, 11.63. MS (ESI-, [M-H]$^-$) m/z: 270.2.

Step C: DCM (240 mL), (N-(3-cyano-4-fluorophenyl)-1,2,4-trimethyl-1H-pyrrol-3-carboxamide (5.0 g) and monoethyl chlorooxalate (7.55 g) were added to a 500 mL single-neck flask under nitrogen atmosphere. Aluminum chloride (12.29 g) was added in portions in an ice bath. After the addition, the reaction system was warmed to room temperature and reacted for 15.0 h. After the reaction was completed, the mixture was slowly poured into 300 mL of ice water to quench the reaction and extracted with DCM (2×300 mL). The organic phases were combined, washed with saturated aqueous sodium chloride solution, dried over anhydrous sodium sulfate and filtered under vacuum. The filtrate was concentrated by rotary evaporation at reduced pressure to remove the solvent. Ethyl acetate (45 mL) was added to the resulting crude product, and the mixture was slurried at room temperature for 1.0 h and filtered under vacuum. The filter cake was dried under vacuum to obtain ethyl 2-(4-((3-cyano-4-fluorophenyl)carbamoyl)-1,3,5-trimethyl-1H-pyrrol-2-yl)-2-oxoacetate (4.25 g). MS (ESI-, [M-H]$^-$) m/z: 370.2.

Step D: Methanol (30 mL), ethyl 2-(4-((3-cyano-4-fluorophenyl)carbamoyl)-1,3,5-trimethyl-1H-pyrrol-2-yl)-2-oxoacetate (4.00 g) and a solution of sodium hydroxide (0.862 g) in water (30 mL) were added to a 100 mL single-neck flask in an ice bath. After the addition, the reaction system was warmed to room temperature and reacted for 2.0 h. Water (200 mL) and DCM (150 mL) was added to the reaction solution. The mixture was separated and the organic phase was discarded. The aqueous phase was adjusted to about pH 2 by adding concentrated hydrochloric acid, and extracted with ethyl acetate (2×150 mL). The organic phases were combined, washed with saturated aqueous sodium chloride solution, dried over anhydrous sodium sulfate and filtered under vacuum. The filtrate was concentrated by evaporation at reduced pressure to remove the solvent, so as to obtain 2-(4-(3-cyano-4-fluorophenyl)carbamoyl)-1,3,5-trimethyl-1H-pyrrol-2-yl)-2-oxoacetic acid (3.25 g). $^1$H-NMR (500 MHz, DMSO-d$_6$): δ 10.32 (s, 1H), 8.19-8.21 (m, 1H), 7.93-7.97 (m, 1H), 7.52 (t, J=9.0 Hz, 1H), 3.81 (s, 3H), 2.36 (s, 3H), 2.27 (s, 3H). $^{13}$C-NMR (125 MHz, DMSO-d$_6$): δ 178.85, 167.79, 163.98, 159.67, 157.66, 141.31, 136.80, 130.95, 127.26, 123.84, 117.60, 114.43, 10±0.41, 60.21, 33.73, 21.22, 14.55.

Step E: DMF (3.0 mL), 2-(4-(3-cyano-4-fluorophenyl)carbamoyl)-1,3,5-trimethyl-1H-pyrrol-2-yl)-2-oxoacetic acid (100 mg), HATU (138 mg) and DIPEA (83 mg) were sequentially added to a 50 mL single-neck flask, then (S)-1,1,1-trifluoroisopropylamine hydrochloride (56 mg) was added. The reaction system was stirred at room temperature for 2.5 h. Water (50 mL) was added to the reaction solution. The mixture was extracted with ethyl acetate (2×50 mL). The organic phases were combined, washed with saturated aqueous sodium chloride solution and dried over anhydrous sodium sulfate. The solvent was removed by evaporation at reduced pressure, and the resulting crude product was separated by silica gel column chromatography (PE:EA=1:1) to obtain (S)—N-(3-cyano-4-fluorophenyl)-1,2,4-trimethyl-5-(2-oxo-2-((1,1,1-trifluoropropan-2-yl)amino)acetyl)-1H-pyrrol-3-carboxamide (54 mg). $^1$H-NMR (500 MHz, DMSO-d$_6$): δ 10.31 (s, 1H), 9.38 (d, J=9.0 Hz, 1H), 8.19-8.21 (m, 1H), 7.93-7.97 (m, 1H), 7.51 (t, J=9.5 Hz, 1H), 4.68-4.75 (m, 1H), 3.79 (s, 3H), 2.36 (s, 3H), 2.21 (s, 3H), 1.31 (d, J=7.0 Hz, 3H). $^{13}$C-NMR (125 MHz, DMSO-d$_6$): δ 180.80, 167.24, 164.08, 159.66, 157.65, 140.92, 136.82, 130.81, 127.31, 125.02, 123.81, 120.71, 117.58, 114.44, 10±0.40, 46.04, 33.66, 13.75, 11.57. MS (ESI-, [M-H]$^-$) m/z: 437.3.

Figure 2:
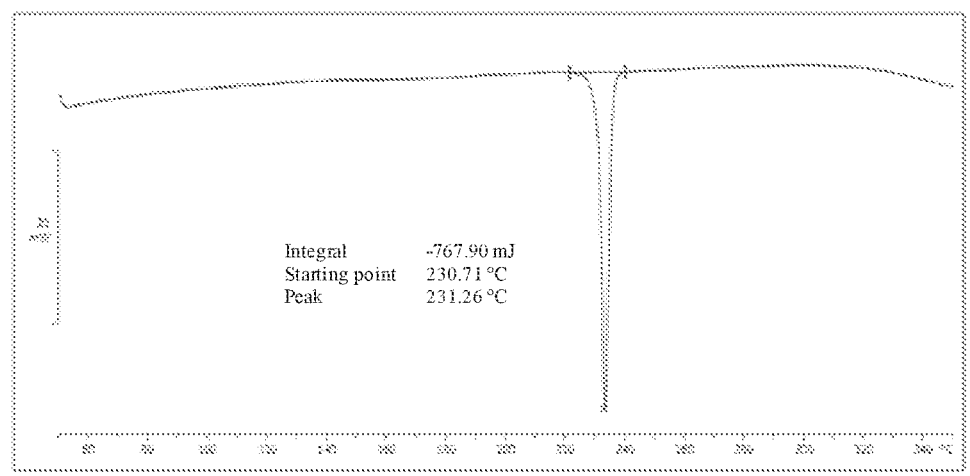
FIG. 2 is a DSC pattern of the crystalline form I of the compound of formula I.

Example 2. Preparation of Crystalline Form I of Compound of Formula I 100 g of the compound of formula I was added to 500 mL of anhydrous methanol at room temperature for recrystallization. A large amount of white solid was precipitated. The mixture was filtered, and the filter cake was rinsed with anhydrous methanol and dried by air blasting at 50° C. for 8 h to obtain an off-white solid of the crystalline form I of the compound of formula I (79 g). The sample was subjected to XRPD as shown in FIG. 1 and to DSC as shown in FIG. 2.

Example 3. Preparation of Crystalline Form I of Compound of Formula I

At room temperature, 400 mg of the compound of formula I was added to 5 mL of acetonitrile. The mixture was stirred for 20 min to give a clarified solution, then 25 mL of purified water was added dropwise. A large amount of white solid was precipitated. The mixture was filtered under vacuum, and the filter cake was dried by air blasting at 60° C. for 6 h to obtain an off-white solid of the crystalline form I of the compound of formula I (303 mg).

Example 4. Preparation of Crystalline Form II of Compound of Formula I

Figure 3:
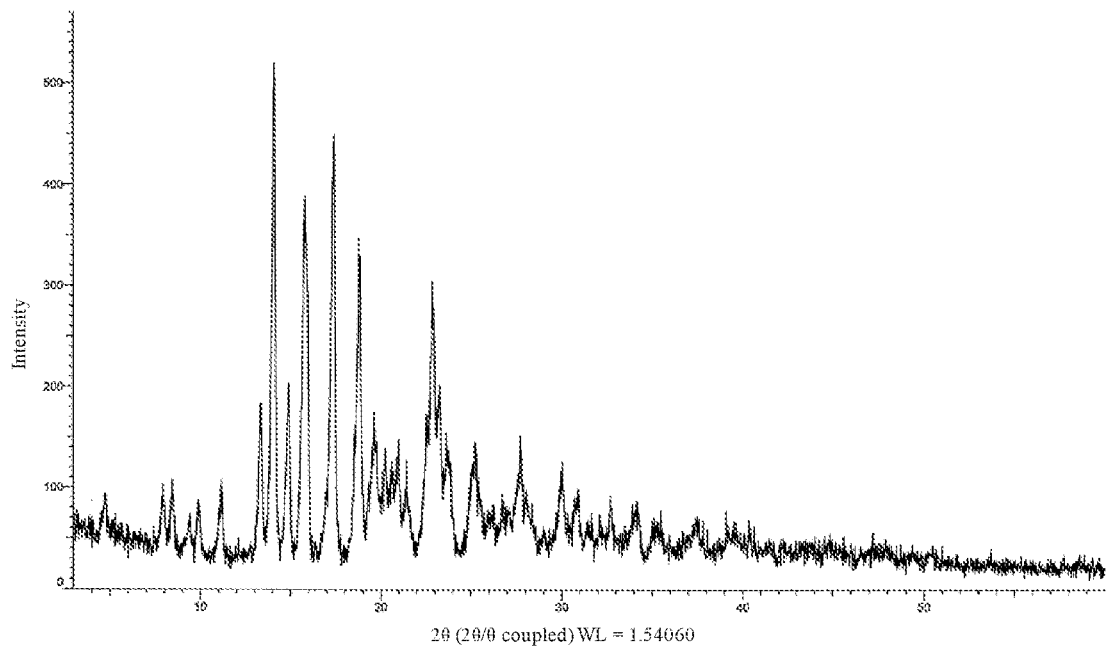
FIG. 3 is an XRPD pattern of a crystalline form II of the compound of formula I.
Figure 4:
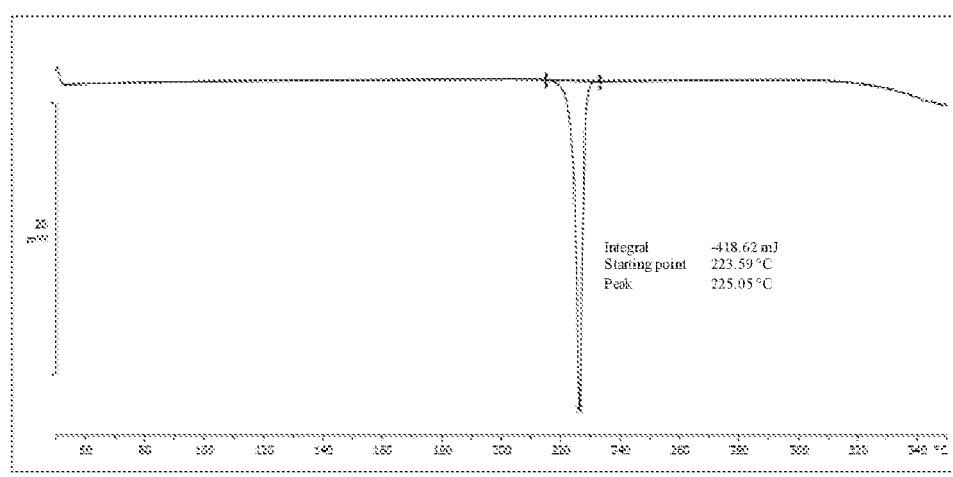
FIG. 4 is a DSC pattern of the crystalline form II of the compound of formula I.

At room temperature, 10 g of the compound of formula I was added to 200 mL of acetone. The mixture was stirred to give a clarified solution, then 250 mL of purified water was slowly and dropwise added. A large amount of white solid was precipitated. The mixture was filtered under vacuum, and the filter cake was dried by air blasting at 60° C. for 7 h to obtain an off-white solid of the crystalline form II of the compound of formula I (7.2 g). The sample was subjected to XRPD as shown in FIG. 3 and to DSC as shown in FIG. 4.

Experimental Example 1. Stability Assay of Crystalline Form 1.1. Preparation of Samples The crystalline form I of the compound of formula I prepared in Example 2 and the crystalline form II of the compound of formula I prepared in Example 4, each of 500 mg, were separately placed in dry and clean containers, and evenly spread in thin layers as test samples. The samples were completely exposed to experimental conditions of influential factors (40° C., 60° C., 75% RH, 92.5% RH, high temperature and high humidity (40° C., 75% RH)). Samples were taken for analysis on day 10 and day 30. The samples were completely exposed to illumination (visible light of 1,200,000 Lux·hr, UV of 216 W·hr/m$^2$) at room temperature.

1.2. Instruments and Analytical Methodology

Chromatographic column: Agilent AdvanceBio Peptide C18 (4.6 mm×150 mm, 3.5 μm).

The water content was measured by a Mettler V20 system.

1.3. Preparation of Sample Solution

About 10 mg of the sample was dissolved with an appropriate amount of a mixed diluent of acetonitrile-water (70:30) for content assay of related substance.

TABLE 3-1

Results of stability assay for crystalline form I

| Observation items | Day 0 | High temperature (40° C.) | | High temperature (60° C.) | | High humidity (75% RH) | | High humidity (92.5% RH) | | Illumination | High temperature and high humidity (40° C., 75% RH) | |
|---|---|---|---|---|---|---|---|---|---|---|---|---|
| | | Day 10 | Day 30 | Day 10 | Day 30 | Day 10 | Day 30 | Day 10 | Day 30 | Day 10 | Day 10 | Day 30 |
| Related substance[a] (%) | 0.55 | 0.66 | 0.63 | 0.66 | 0.60 | 0.72 | 0.66 | 0.69 | 0.66 | 0.63 | 0.64 | 0.64 |
| Water (%) | 0.27 | 0.18 | 0.19 | 0.20 | 0.18 | 0.19 | 0.20 | 0.21 | 0.26 | 0.16 | 0.17 | 0.22 |

[a]Related substance refers to the total impurities.

The results in Table 3-1 showed that the related substance and water in the crystalline form I are stable under the aforementioned observation items, demonstrating that the crystalline form has good stability at high humidity, at high temperature or under illumination.

TABLE 3-2

Results of stability assay for crystalline form II

| Observation items | Day 0 | High temperature (40° C.) | | High temperature (60° C.) | | High humidity (75% RH) | | High humidity (92.5% RH) | | Illumination | High temperature and high humidity (40° C., 75% RH) | |
|---|---|---|---|---|---|---|---|---|---|---|---|---|
| | | Day 10 | Day 30 | Day 10 | Day 30 | Day 10 | Day 30 | Day 10 | Day 30 | Day 10 | Day 10 | Day 30 |
| Related substance[b] (%) | 0.24 | 0.22 | 0.24 | 0.22 | 0.24 | 0.23 | 0.25 | 0.23 | 0.24 | 0.27 | 0.24 | 0.24 |
| Water (%) | 0.22 | 0.20 | 0.19 | 0.18 | 0.18 | 0.22 | 0.21 | 0.22 | 0.21 | 0.22 | 0.24 | 0.21 |

[b]Related substance refers to the total impurities.

The results in Table 3-2 showed that the related substance and water in the crystalline form II are stable under the aforementioned observation items, demonstrating that the crystalline form has good stability at high humidity, at high temperature or under illumination.

Experimental Example 2. In-Vitro Activity Study 2.1. In-Vitro Inhibitory Activity Against HBV DNA in Cells A vial of HepG2.2.15 cells (Wuhan Institute of Virology) or HepAD38 cells in good condition and at logarithmic growth phase was washed once with 5 mL of PBS. 3 mL of pancreatin was added. The cells were digested at room temperature for 5 min, then 2 mL of pancreatin was discarded. The cells were further digested in a cell incubator for 10 min, and observed under a microscope (whether the cells are round in shape, and whether the cells are separated or adhered). 10 mL of complete medium was added to terminate the digestion. The cells was mixed using a pipette to obtain a single cell suspension. 10 µL of the cell suspension was loaded on a cell counter for counting, and diluted with the complete medium to adjust the cell density to $1 \times 10^5$ cells/mL. The cells were seeded on a 24-well plate (pre-coated with 50 µg/mL Collagen I solution) at 1 mL/well using a multi-channel pipette and cultured in a thermostatic $CO_2$ incubator for 48 h.

A solution of the compound dissolved in DMSO was diluted to 10 concentrations in a 2-fold gradient using complete medium. The cells were treated with the compound for 6 days with the media containing the compound refreshed every 72 h. The supernatant was discarded. 300 µL of lysis buffer (10 mM Tris-HCl, 1 mM EDTA, 1% NP-40) was added to each well. After the cells were lysed at room temperature for 10 min, DNA was extracted. HBV DNA in the intracellular viral capsid was measured by real-time fluorescent quantitative PCR. The inhibition rate was calculated according to the Ct value, and the $EC_{50}$ value was calculated by four-parameter fitting. The results are shown in Table 4 and Table 5.

TABLE 4

Results of anti-HBV activity assay in HepAD38 cells

| Compound | $EC_{50}$ |
|---|---|
| Compound of formula I | $EC_{50} \leq 10$ nM |

TABLE 5

Results of anti-HBV activity assay in HepG2.2.15 cells

| Compound | $EC_{50}$ |
|---|---|
| Compound of formula I | $EC_{50} \leq 10$ nM |

2.2. In Vitro Cytotoxicity

A vial of HepG2.2.15 cells (Wuhan Institute of Virology) or HepAD38 cells in good condition and at logarithmic growth phase was washed once with 5 mL of PBS. 2 mL of pancreatin was added. The cells were incubated in a cell incubator for digestion, and observed at times under a microscope. 1 mL of pancreatin was discarded when the cells just fell off, leaving the residual liquid only. The cells were further incubated in the incubator at 37° C. for 8-15 min of digestion and observed under a microscope (whether the cells are round in shape, and whether the cells are separated or adhered). 5 mL of MEM medium was added for cell resuspension. The cell suspension was loaded on a cell counter for counting, and diluted with the complete medium to adjust the cell density to $2\times10^5$ cells/mL. The cells were seeded on a 96-well plate (pre-coated with 50 µg/mL Collagen I solution) at 100 µL/well using a multi-channel pipette and cultured in a thermostatic $CO_2$ incubator for 24 h. The compound was added, and the medium containing the compound was refreshed every 3 days. A medium containing 0.5% of DMSO but no compound was added to the control wells, and control wells of basal medium were set. After 6 days of treatment, CCK-8 was added at 10 µL/well, and after 1-2 h, the absorbance at 450 nm was measured with a plate reader. The inhibition rate and $CC_{50}$ were calculated. The results are shown in Table 6.

TABLE 6

| Cells | $CC_{50}(\mu M)$ | Compound |
|---|---|---|
| HepAD38 | >100 | Compound of formula I |
| HepG2.2.15 | >100 | Compound of formula I |

2.3. CYP450 Enzyme Induction Study

A final incubation system of 500 µL contained 50 µL of liver microsomes (protein concentration: 0.2 mg/mL, Corning), 1 µL of mixed specific substrates of CYP450 (CYP1A2, CYP2B6, CYP2C9, CYP2C19, CYP2D6, CYP3A4), 398 µL of PBS (pH 7.4), 1 µL of specific positive inhibitor (positive control) or test compound (in acetonitrile) and 50 µL of NADPH+$MgCl_2$. Samples were prepared in duplicate of 0.5 mL for each CYP450 subtype. For each tube, the 450 µL mixed solution of substrates and enzyme and the NADPH solution were separately pre-incubated at 37° C. for 5 min. The 50 µL mixed solution of NADPH+$MgCl_2$ was added for reaction. At 30 min, 50 µL of the mixture was taken and 300 µL of glacial acetonitrile containing an internal standard was added to terminate the reaction. Additionally, 2 blanks of 500 µL each were prepared in parallel without adding NADPH as the negative control group.

Sample pretreatment: 300 µL of glacial acetonitrile containing an internal standard was added to 50 µL of the incubated sample for precipitation. The mixture was vortexed for 5 min, and centrifuged (12000 rpm, 4° C.) for 10 min. 75 µL of supernatant was taken and diluted with 75 µL of ultrapure water. After being mixed well, 1 µL of the resulting sample was injected for analysis. The results are shown in Table 7.

TABLE 7

| Compound | Each subtype $IC_{50}$ (µM) | | | | | |
|---|---|---|---|---|---|---|
| | 3A4 | 2D6 | 2C19 | 2C9 | 2B6 | 1A2 |
| Compound of formula I | >200 | 223.5 | 60.0 | 79.7 | 145.6 | 46.4 |

2.4. Plasma Protein Binding Assay

Preparation of plasma samples: 5 µL of test compound solution or positive control was added to 495 µL of blank plasma of various species (mouse, rat, dog, monkey and human) to obtain plasma sample solutions at plasma concentrations of 1 µM and 10 µM (in acetonitrile).

The pretreated dialysis membrane was loaded on a high-throughput equilibrium dialysis system. 100 µL of the plasma sample solution and PBS buffer were added to the two sides (sample side and buffer side) of the dialysis membrane respectively (n=3). The system was sealed with a patch and incubated at 37° C. overnight (100 rpm) to achieve dialysis equilibrium. 50 µL samples were taken from the sample side and the buffer side, and the reaction was terminated with glacial acetonitrile containing an internal standard.

Sample pretreatment: 450 µL of glacial acetonitrile containing an internal standard was added to 50 µL of the sample from the plasma side for precipitation. The mixture was vortexed for 5 min, and centrifuged (12000 rpm, 4° C.) for 10 min. 75 µL of supernatant was taken and diluted with 75 µL of ultrapure water. After being mixed well, 1 µL of the resulting sample was injected for analysis; 250 µL of glacial acetonitrile containing an internal standard was added to 50 µL of the sample from the PBS side for precipitation. The mixture was vortexed for 5 min, and centrifuged (12000 rpm, 4° C.) for 10 min. 75 µL of supernatant was taken and diluted with 75 µL of ultrapure water. After being mixed well, 2 µL of the resulting sample was injected for analysis. The results are shown in Table 8.

TABLE 8

| Compound | Concentrations | Binding rate (%) | | | | |
|---|---|---|---|---|---|---|
| | | Human | Rat | Mouse | Dog | Monkey |
| Compound of formula I | 1 µM | 94.0 | 82.0 | 75.3 | 85.9 | 90.7 |
| | 10 µM | 93.7 | 79.2 | 74.5 | 85.9 | 90.6 |

Experimental Example 3. In Vitro Stability in Liver Microsome

A final incubation system of 300 µL contained 30 µL of liver microsomes (protein concentration: 0.15 mg/mL), 30 µL of NADPH+$MgCl_2$, 3 µL of substrate (in acetonitrile) and 237 µL of PBS. Samples were prepared in duplicate of 0.3 mL for each specie. For each tube, the 270 µL mixed solution of substrates and enzyme and the NADPH solution were separately pre-incubated at 37° C. for 5 min. The 30 µL mixed solution of NADPH+$MgCl_2$ was added for reaction. 50 µL samples were taken at 0 min, 10 min, 30 min and 60 min, and 300 µL of glacial acetonitrile containing an internal standard was added to the samples to terminate the reaction.

Sample pretreatment: 300 µL of glacial acetonitrile containing internal standard diazepam was added to 50 µL of the incubated sample for precipitation. The mixture was vortexed for 5 min, and centrifuged (12000 rpm, 4° C.) for 10 min. 75 µL of supernatant was added to a 96-well plate and diluted with 75 μL of ultrapure water. After being mixed well, 0.5 μL of the resulting sample was injected to a LC-MS/MS system for analysis. The results are shown in Table 9.

TABLE 9

| | In Vitro stability in liver microsome | | |
|---|---|---|---|
| | Residual content after 60 min (%) | | |
| Compound | Human liver microsome | Rat liver microsome | Mouse liver microsome |
| Compound of formula I | 78.8 | 65.0 | 67.1 |

Experimental Example 4. Solubility in PBS at pH 7.4

A final system of 1000 μL contained 990 μL of PBS at pH 7.4 and 10 μL of the test compound (in acetonitrile). After standing at 25° C. for 16 h, the mixture was centrifuged (12000 rpm, room temperature) for 10 min. 20 μL of the supernatant was taken, and the reaction was terminated with 400 μL of acetonitrile containing an internal standard (20 ng/mL diazepam). 30 μL of supernatant was taken and diluted with 150 μL of 50% aqueous acetonitrile solution. After being mixed well, 0.5 μL of the resulting sample was injected for analysis. The results are shown in Table 10.

TABLE 10

| Compound | Solubility (μM) |
|---|---|
| Compound of formula I | 8.1 |

Experimental Example 5. In Vivo Drug Efficacy in Animals 5.1. Evaluation of Antiviral Effect in AAV Mouse Model Male C57BL/6 mice (Shanghai Lingchang Biotechnology Co., Ltd.) aged 6-8 weeks were selected, and rAAV8-1.3HBV virus (FivePlus, Beijing, adr subtype) was injected into the C57BL/6 mice via tail veins at a dose of $1 \times 10^{11}$ vg. Blood was collected from the orbit at week 2 and week 4 after the virus was injected. Serum was separated, and the expression level of HBeAg and HBsAg and the copy number of HBV DNA in serum were measured to determine whether the model was successfully constructed or not. Combining the quantitative detection results of serological HBeAg, HBsAg and HBV DNA, mice with the expression levels over $1 \times 10^4$ IU/mL for HBV DNA, $1 \times 10^3$ NCU/mL for HBeAg and $1 \times 10^3$ ng/mL for HBsAg were selected. The mice were divided into a blank control group, a vehicle control group and a test compound group. Mice were administered by oral gavage once daily for 2-3 weeks. During the study, blood was collected from the orbit every other week, and serum was separated. The content of DNA was detected by fluorescence quantitative PCR. The results are shown in Table 11.

TABLE 11

| Reduction (log10) of HBV DNA level in serum (24 days after administration, 30 mpk) | | | | |
|---|---|---|---|---|
| Compound | Day 7 | Day 14 | Day 21 | Day 28 |
| Compound of formula I | 2.42 | 3.46 | 5.08 | 2.48 |

5.2. Evaluation of Antiviral Effect in HDI Mouse Model

Purified recombinant plasmid pHBV1.3 (10 μg) was dissolved in PBS and then injected into male C57BL/6 mice (Shanghai Lingchang Biotechnology Co., Ltd.) aged 6-8 weeks via tail veins within 3-8 s in an amount of about 10% of the body weight. 24 h after the plasmid was injected, blood was collected from the orbit and serum HBV DNA was detected. Mice with homogeneous serum DNA were selected and divided into a blank control group, a vehicle control group and a test compound group. Mice were administered with a dose of 30 mg/kg by oral gavage once daily for 6 days. Serum was taken on days 1, 3, 5 and 7 after injection. The mice were sacrificed and liver tissues were collected on day 7. The copy number of HBV DNA in serum and liver was determined by a fluorescence quantitative PCR method. The results are shown in Table 12.

TABLE 12

| Compound | Reduction (log10) of HBV DNA level in serum on day 5 |
|---|---|
| Compound of formula I | 2.17 |

Experimental Example 6. In Vivo Pharmacokinetics 6.1. Pharmacokinetic (PK) Study in Rats SD rats (B&K Universal, Shanghai) of 180-220 g were randomized into groups of 3 after 3-5 days of acclimatization and administered with the compounds at a dose of 20 mg/kg by oral gavage.

The animals to be tested (SD rats) were fasted for 12 h before administration and fed 4 h after administration, and had free access to water before, after and during the experiment.

After administration, about 0.2 mL of blood was collected from the orbit at 0 min, 15 min, 30 min, 1 h, 2 h, 4 h, 6 h, 8 h, 10 h, 24 h, 30 h and 48 h. After anticoagulation with EDTA-K2, the blood samples were transferred to a centrifuge at 4° C. within 30 min and centrifuged at 4000 rpm for 10 min to separate the plasma. All the plasma samples were collected and immediately stored at −20° C. for testing. 50 μL of the plasma sample to be tested and standard curve sample were taken, and 500 μL of acetonitrile solution containing an internal standard (20 mg/mL diazepam) was added. The reaction system was shaken for 5 min and centrifuged at 12,000 rpm for 10 min. 75 μL of supernatant was taken and diluted with 75 μL of ultrapure water.

After being mixed well, 1 μL of the resulting sample was taken for LC/MS/MS analysis. The results are shown in Table 13.

TABLE 13

| Compound Route of administration and dosage | Compound of formula I | |
|---|---|---|
| | IV | PO |
| | 5 mg/kg | 20 mg/kg |
| $T_{1/2}$ (h) | 3.41 | 3.65 |
| Vz (mL/kg) | 914 | NA |
| Cl (mL/h/kg) | 186 | NA |
| $C_{max}$ (ng/mL) | 6274 | 5019 |
| $AUC_{(0-48\ h)}$ (ng*h/mL) | 27082 | 62040 |
| $AUC_{(0-\infty)}$ (ng*h/mL) | 27146 | 62340 |
| F (%) | NA | 57% |

NA denotes not available.

6.2. Pharmacokinetic (PK) Study in Beagle Dogs

Beagle dogs of 9-11 kg were randomized into two groups of 3 and administered with the compound of formula I at a dose of 5 mg/kg by oral gavage.

The animals to be tested (beagle dogs) were fasted for 12 h before administration and fed 4 h after administration, and had free access to water before, after and during the experiment.

After oral gavage, about 0.5 mL of whole blood was collected from the left forelimb vein in a vacutainer with EDTA-K2 for anticoagulation at 0 min, 15 min, 30 min, 1 h, 2 h, 4 h, 6 h, 8 h, 10 h, 24 h, 48 h and 72 h. The blood samples were transferred to a centrifuge at 4° C. within 30 min and centrifuged at 4000 rpm for 10 min to separate the plasma. All the plasma samples were collected and immediately stored at –20° C. for testing. All the plasma samples were collected and immediately stored at –20° C. for testing. 50 µL of the plasma sample to be tested and standard curve sample were taken, and 500 µL of acetonitrile solution containing an internal standard (20 mg/mL diazepam) was added. The reaction system was shaken for 5 min and centrifuged at 12,000 rpm for 10 min. 75 µL of supernatant was taken and diluted with 75 µL of ultrapure water.

After being mixed well, 1 µL of the resulting sample was taken for LC/MS/MS analysis. The results are shown in Table 14.

TABLE 14

| Compound Route of administration and dosage | Compound of formula I PO 5 mg/kg |
|---|---|
| $T_{max}$ (h) | 1.67 |
| $C_{max}$ (ng/mL) | 1282 |
| $AUC_{(0-72\ h)}$ (ng*h/mL) | 61881 |
| $AUC_{(0-\infty)}$ (ng*h/mL) | 162075 |
| $T_{1/2}$ (h) | 105.2 |
| MRT(0-t) (h) | 32.9 |

The invention claimed is:

1. A crystalline form of a compound of formula I,

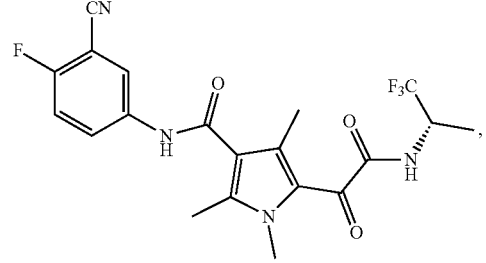

I wherein the crystalline form has characteristic diffraction peaks in an X-ray powder diffraction (XRPD) pattern at three or more of the following 2θ: 9.21±0.20°, 16.47±0.20°, 18.11±0.20°, 24.48±0.20°, 26.79±0.20°, or wherein the crystalline form has characteristic diffraction peaks in an XRPD pattern at three or more of the following 2θ: 14.09±0.20°, 15.81±0.20°, 17.40±0.20°, 18.81±0.20° and 22.91±0.2°.

2. The crystalline form of the compound of formula I according to claim 1, wherein the crystalline form has characteristic diffraction peaks in an X-ray powder diffraction pattern at the following 2θ: 9.21±0.20°, 16.47±0.20°, 18.11±0.20°, 24.48±0.20° and 26.79±0.20°.

3. The crystalline form of the compound of formula I according to claim 2, wherein the XRPD pattern of the crystalline form is shown in FIG. 1.

4. The crystalline form of the compound of formula I according to claim 2, wherein the crystalline form has an endothermic peak in a DSC curve at 231.26±5° C.

5. The crystalline form of the compound of formula I according to claim 1, wherein the crystalline form has characteristic diffraction peaks in an X-ray powder diffraction pattern at the following 2θ: 14.09±0.20°, 15.81±0.20°, 17.40±0.20°, 18.81±0.20° and 22.91±0.2°.

6. The crystalline form of the compound of formula I according to claim 5, wherein the XRPD pattern of the crystalline form is shown in FIG. 3.

7. The crystalline form of the compound of formula I according to claim 5, wherein the crystalline form has an endothermic peak in a DSC curve at 225.05±5° C.

8. A crystalline form composition, comprising the crystalline form of the compound of formula I according to claim 1, wherein the crystalline form accounts for 50% or more of the weight of the crystalline form composition.

9. A pharmaceutical composition, comprising a therapeutically effective amount of the crystalline form of the compound of formula I according to claim 1.

10. A method for treating a disease caused by hepatitis B virus infection, comprising administering to a mammal in need of such treatment a therapeutically effective amount of the crystalline form of the compound of formula I according to claim 1.

11. The crystalline form of the compound of formula I according to claim 2, wherein the crystalline form has characteristic diffraction peaks in an X-ray powder diffraction pattern at the following 2θ: 9.21±0.20°, 12.72±0.20°, 15.71±0.20°, 16.47±0.20°, 18.11±0.20°, 19.79±0.20°, 24.48±0.20° and 26.79±0.20°.

12. The crystalline form of the compound of formula I according to claim 2, wherein the crystalline form has characteristic diffraction peaks in an X-ray powder diffraction pattern at the following 2θ: 9.21±0.20°, 10.44±0.20°, 12.72±0.20°, 15.06±0.20°, 15.71±0.20°, 16.47±0.20°, 18.11±0.20°, 19.79±0.20°, 20.46±0.20°, 24.48±0.20°, 26.79±0.20° and 31.46±0.20°.

13. The crystalline form of the compound of formula I according to claim 2, wherein the crystalline form has characteristic diffraction peaks in an X-ray powder diffraction pattern at the following 2θ: 9.21±0.20°, 9.68±0.20°, 10.44±0.20°, 12.72±0.20°, 15.06±0.20°, 15.71±0.20°, 16.47±0.20°, 18.11±0.20°, 19.79±0.20°, 20.46±0.20°, 24.48±0.20°, 26.02±0.20°, 26.79±0.20°, 27.67±0.20° and 31.46±0.20°.

14. The crystalline form of the compound of formula I according to claim 2, wherein the crystalline form has characteristic diffraction peaks in an X-ray powder diffraction pattern at the following 2θ: 4.86±0.20°, 9.21±0.20°, 9.68±0.20°, 10.44±0.20°, 12.47±0.20°, 12.72±0.20°, 15.06±0.20°, 15.71±0.20°, 16.47±0.20°, 18.11±0.20°, 18.74±0.20°, 19.19±0.20°, 19.79±0.20°, 20.46±0.20°, 20.94±0.20°, 21.65±0.20°, 21.96±0.20°, 23.12±0.20°, 24.48±0.20°, 26.02±0.20°, 26.79±0.20°, 27.67±0.20°, 29.36±0.20°, 31.46±0.20° and 34.17±0.20°.

15. The crystalline form of the compound of formula I according to claim 5, wherein the crystalline form has characteristic diffraction peaks in an X-ray powder diffraction pattern at the following 2θ: 8.45±0.20°, 13.35±0.20°, 14.09±0.20°, 14.90±0.20°, 15.81±0.20°, 17.40±0.20°, 18.81±0.20°, 19.64±0.20° and 22.91±0.20°.

16. The crystalline form of the compound of formula I according to claim 5, wherein the crystalline form has characteristic diffraction peaks in an X-ray powder diffraction pattern at the following 2θ: 8.45±0.20°, 11.15±0.20°, 13.35±0.20°, 14.09±0.20°, 14.90±0.20°, 15.81±0.20°, 17.40±0.20°, 18.81±0.20°, 19.64±0.20°, 20.97±0.20°, 22.91±0.20°, 23.68±0.20° and 25.24±0.20°.

17. The crystalline form of the compound of formula I according to claim 5, wherein the crystalline form has characteristic diffraction peaks in an X-ray powder diffraction pattern at the following 2θ: 8.45±0.20°, 11.15±0.20°, 13.35±0.20°, 14.09±0.20°, 14.90±0.20°, 15.81±0.20°, 17.40±0.20°, 18.81±0.20°, 19.64±0.20°, 20.25±0.20°, 20.97±0.20°, 21.42±0.20°, 22.91±0.20°, 23.68±0.20°, 25.24±0.20°, 27.72±0.20° and 30.00±0.20°.

18. The crystalline form of the compound of formula I according to claim 5, wherein the crystalline form has characteristic diffraction peaks in an X-ray powder diffraction pattern at the following 2θ: 4.74±0.20°, 7.94±0.20°, 8.45±0.20°, 9.40±0.20°, 9.91±0.20°, 11.15±0.20°, 13.35±0.20°, 14.09±0.20°, 14.90±0.20°, 15.81±0.20°, 17.40±0.20°, 18.81±0.20°, 19.64±0.20°, 20.25±0.20°, 20.97±0.20°, 21.42±0.20°, 22.91±0.20°, 23.68±0.20°, 25.24±0.20°, 27.72±0.20° and 30.00±0.20°.

\* \* \* \* \*